(12) United States Patent
Sakakura

(10) Patent No.: US 8,079,346 B2
(45) Date of Patent: *Dec. 20, 2011

(54) OXYGEN ACTIVATING MATERIAL, COMBUSTION EFFICIENCY IMPROVING MATERIAL, PLANT GROWTH PROMOTING MATERIAL, AEROBIC MICROORGANISM ACTIVATING MATERIAL, ANIMAL GROWTH PROMOTING AND ACTIVATING MATERIAL, MUSCLE SOFTENING MATERIAL, RUST REMOVING AND PREVENTING MATERIAL, AND OXYGEN ACTIVATING METHOD

(76) Inventor: Yasuo Sakakura, Saitama (JP)

( * ) Notice: Subject to any disclaimer, the term of this patent is extended or adjusted under 35 U.S.C. 154(b) by 972 days.

This patent is subject to a terminal disclaimer.

(21) Appl. No.: 11/916,692

(22) PCT Filed: Jun. 28, 2005

(86) PCT No.: PCT/JP2005/012298
§ 371 (c)(1),
(2), (4) Date: Dec. 6, 2007

(87) PCT Pub. No.: WO2007/000828
PCT Pub. Date: Jan. 4, 2007

(65) Prior Publication Data
US 2010/0059361 A1  Mar. 11, 2010

(51) Int. Cl.
*F02M 33/00* (2006.01)
(52) U.S. Cl. ........................................ 123/536
(58) Field of Classification Search .......... 123/536–539; 148/525, 529; 134/1
See application file for complete search history.

(56) References Cited

U.S. PATENT DOCUMENTS

| 6,136,429 A * | 10/2000 | Saito ........................ 428/323 |
| 6,444,049 B1 | 9/2002 | Yamashita et al. |
| 2005/0274607 A1 | 12/2005 | Kitada et al. |

FOREIGN PATENT DOCUMENTS

| CN | 1099468 C | 5/1999 |
| JP | 57-82106 | 5/1982 |
| JP | 60-087849 | 5/1985 |
| JP | 62297454 A * | 12/1987 |
| JP | 05-337192 | 12/1993 |
| JP | 09-013147 | 1/1997 |
| JP | 09-327522 | 12/1997 |
| JP | 10-113695 | 5/1998 |
| JP | 10-121222 | 5/1998 |
| JP | 10-195435 | 7/1998 |
| JP | 10-290094 | 10/1998 |
| JP | 11-092106 | 4/1999 |
| JP | 2001-050121 | 2/2001 |
| JP | 2002-507251 | 3/2002 |
| JP | 2003-137703 | 5/2003 |
| JP | 2003-187812 | 7/2003 |
| JP | 2003-245365 | 9/2003 |
| KR | 1997-012142 | 11/1998 |
| KR | 1020020018740 A | 9/2002 |
| WO | 99/01585 | 1/1999 |
| WO | 99/23265 | 5/1999 |
| WO | 2004/031450 A1 | 4/2004 |

OTHER PUBLICATIONS

Supplementary European Search Report which issued in connection with corresponding European Application No. 05765450.1 on Mar. 30, 2009.
Examination Report which issued in connection with corresponding European Patent Application No. 05765450.1 on Sep. 10, 2009.

* cited by examiner

*Primary Examiner* — Marguerite McMahon
(74) *Attorney, Agent, or Firm* — Clark Hill PLC

(57) ABSTRACT

The invention provides an oxygen activating material, which includes as a major constituent an iron-semiconductor alloy containing iron and semiconductor components. A combustion efficiency improving material, a plant growth promoting material, an aerobic microorganism activating material, an animal growth promoting and activating material, a muscle softening material, and a rust removing and preventing material are also provided. In addition an oxygen activating method is also provided.

2 Claims, No Drawings

OXYGEN ACTIVATING MATERIAL, COMBUSTION EFFICIENCY IMPROVING MATERIAL, PLANT GROWTH PROMOTING MATERIAL, AEROBIC MICROORGANISM ACTIVATING MATERIAL, ANIMAL GROWTH PROMOTING AND ACTIVATING MATERIAL, MUSCLE SOFTENING MATERIAL, RUST REMOVING AND PREVENTING MATERIAL, AND OXYGEN ACTIVATING METHOD

RELATED/PRIORITY APPLICATION

This application is a National Phase filing regarding International Application No. PCT/JP2005/012298, filed on Jun. 28, 2005.

TECHNICAL FIELD

The present invention relates to: an oxygen activating material for activating oxygen to improve the reactivity of oxygen; a combustion efficiency improving material for improving the combustion efficiency of fuels such as gasoline; a plant growth promoting material for promoting the growth of plants; an aerobic microorganism activating material for activating or breeding aerobic microorganisms; an animal growth promoting and activating material for promoting the growth of animals and activating the motion of animals; a muscle softening material for loosening muscles to soften them; a rust removing and preventing material for removing rust and preventing occurrences of rust; and an oxygen activating method for activating oxygen.

BACKGROUND ART

Silicon iron, which is an alloy of iron and silicon, has been employed widely in the art as a soft-magnetic metal material in various uses such as motor iron cores and magnetic shield materials (JP-A 8-275413 and 6-37479). It also has been used as a deoxidizer in steel-making industries. There are other various semiconductors than silicon, such as germanium and selenium, which may be alloyed with iron.

Alloys containing iron and semiconductor components, such as silicon iron, have properties that have not yet been elucidated, and may be utilized in various uses possibly. Therefore, the present invention has an object to find out new uses of iron-semiconductor alloys such as silicon iron.

DISCLOSURE OF INVENTION

The inventor has eagerly repeated studies to achieve the above object and consequently found out that an iron-semiconductor alloy containing iron and semiconductor components has a property of activating oxygen to improve the reactivity thereof. Thus, the present invention provides an oxygen activating material, an oxygen activating agent, or an oxygen activating composition, which includes as a major constituent an iron-semiconductor alloy containing iron and semiconductor components.

The oxygen activating material according to the present invention is capable of activating oxygen and accordingly improving the combustion efficiency in a combustion-based power such as an engine or a combustion-based generator for heat such as a boiler. Thus, the present invention provides a combustion efficiency improving material, a combustion efficiency improving agent, or a combustion efficiency improving composition, which contains the above oxygen activating material or the like.

The oxygen activating material according to the present invention is capable of activating oxygen and accordingly promoting the growth of plants. Thus, the present invention provides a plant growth promoting material, a plant growth promoting agent, or a plant growth promoting composition, which contains the above oxygen activating material or the like. The plants, of which growth can be promoted by the plant growth promoting material according to the present invention, include foliage plants, vegetables, fruits or the like.

The oxygen activating material according to the present invention is capable of activating oxygen and accordingly activating aerobic microorganisms. Thus, the present invention provides an aerobic microorganism activating material, an aerobic microorganism activating agent, or an aerobic microorganism activating composition, which contains the above oxygen activating material or the like. The aerobic microorganism activating material according to the present invention is capable of activating the activity of aerobic microorganisms, breeding aerobic microorganisms, or activating and breeding aerobic microorganisms.

The oxygen activating material according to the present invention is capable of activating oxygen and accordingly promoting the growth of animals and activating the motion of animals. Thus, the present invention provides an animal growth promoting and activating material, an animal growth promoting and activating agent, or an animal growth promoting and activating composition, which contains the above oxygen activating material or the like. The animal growth promoting and activating material according to the present invention is capable of promoting the growth of animals, speeding or activating the motion of animals, or promoting the growth and activating the motion. The animals, of which growth can be promoted by the animal growth promoting and activating material according to the present invention, include mammals, fish and birds.

The oxygen activating material according to the present invention is capable of activating oxygen and accordingly softening muscles. Thus, the present invention provides a muscle softening material, a muscle softening agent, or a muscle softening composition, which contains the above oxygen activating material or the like. The muscle softening material according to the present invention is capable of improving the circulation of blood to loosen stiffness in the shoulder, relieve tension in the waist and loosen muscular pain.

The oxygen activating material according to the present invention is capable of activating oxygen and accordingly removing rust and preventing occurrences of rust. Thus, the present invention provides a rust removing and preventing material, a rust removing and preventing agent, or a rust removing and preventing composition, which contains the above oxygen activating material or the like. The rust removing and preventing material according to the present invention is capable of removing rust and preventing occurrences of rust.

In accordance with the present invention, new uses of iron-semiconductor alloys such as silicon iron can be found in oxygen activating, combustion efficiency improving, plant growth promoting, aerobic microorganism activating, animal growth promoting, animal activating, muscle softening, rust removing, and rust preventing, as described above.

In the oxygen activating material or the like according to the present invention, the semiconductor may include an element semiconductor such as silicon (Si), germanium (Ge), tin (Sn), selenium (Se) and tellurium (Te). It may also include a compound semiconductor such as GaAs, GaP, GaSb, AlN, AlAs, AlSb, InP, InAs, InSb, ZnS, ZnSe, ZnTe, CdS, CdSe, CdTe, AlGaAs, GaInAs, AlInAs, and AlGaInAs. It may further include an oxide semiconductor such as $SnO_2$, ZnO, $Fe_2O_3$, $V_2O_5$, $TiO_2$, NiO, $Cr_2O_3$, $Cu_2O$, $MnO_2$, and MnO. In particular, silicon is preferable.

The oxygen activating material or the like according to the present invention may contain other components, such as nickel (Ni), aluminum (Al), manganese (Mn), carbon (C), chromium (Cr), molybdenum (Mo), titanium (Ti), titanium nitride (TiN), zirconium (Zr), niobium (Nb), and tantalum (Ta), than iron and semiconductor components.

In the oxygen activating material or the like according to the present invention, the content of the semiconductor is preferably 1-20 wt. % and more preferably 1-10 wt. %, and the content of iron is preferably 78-98 wt. % and more preferably 86-96 wt. %.

The fact that the oxygen-activating material or the like according to the present invention activates oxygen in the vicinity of the material can be understood easily from preferable effects exerted on oxygen requiring chemical reactions and biological actions. They include improving the combustion efficiency of fuels, promoting the growth of plants, activating aerobic microorganisms, activating animals, softening muscles, removing rust, and preventing occurrences of rust. In particular, it can be known as well from the fact that the oxygen-activating material according to the present invention could not have activated anaerobic microorganisms.

In the oxygen activating material according to the present invention, different types of atoms cause an electrochemical potential across iron and semiconductor crystals. The electrochemical potential exerts a reverse piezoelectric effect on the semiconductor to cause a mechanical strain. Repeated occurrences of such the strain vibrate the semiconductor, which radiates vibrating-electromagnetic waves to external. The semiconductors contained in the iron-semiconductor alloys have various shapes and sizes and cause various electrochemical potentials, radiating vibrating-electromagnetic waves of various frequencies accordingly. Such the electromagnetic waves attack oxygen having a magnetic moment, exciting oxygen atoms and activating them. In particular, the electromagnetic waves generated from the oxygen activating material can be considered to especially attack oxygen in the vicinity of the material, which performs chemical reactions and contributes to chemical reactions and biological actions.

Irradiation of electromagnetic waves to the oxygen activating material according to the present invention causes severe vibrations of the semiconductor, enhancing vibrating-electromagnetic waves, and further activating nearby oxygen. Thus, the present invention provides an oxygen activating method, which comprises irradiation of electromagnetic waves to the iron-semiconductor alloy containing iron and semiconductor components to activate oxygen in the vicinity of the alloy. The present invention also provides a method, which comprises irradiation of electromagnetic waves to the iron-semiconductor alloy containing iron and semiconductor components to improve the combustion efficiency of fuels in the vicinity of the alloy. The present invention provides a method, which comprises irradiation of electromagnetic waves to the iron-semiconductor alloy containing iron and semiconductor components to promote the growth of plants in the vicinity of the alloy. The present invention provides a method, which comprises irradiation of electromagnetic waves to the iron-semiconductor alloy containing iron and semiconductor components to activate aerobic microorganisms in the vicinity of the alloy. The present invention provides a method, which comprises irradiation of electromagnetic waves to the iron-semiconductor alloy containing iron and semiconductor components to promote the growth of animals and activate animals in the vicinity of the alloy. The present invention provides a method, which comprises irradiation of electromagnetic waves to the iron-semiconductor alloy containing iron and semiconductor components to soften muscles in the vicinity of the alloy. The present invention provides a method, which comprises irradiation of electromagnetic waves to the iron-semiconductor alloy containing iron and semiconductor components to remove rust and prevent occurrences of rust in the vicinity of the alloy. The present invention further provides an oxygen activating material, including as a major constituent an iron-semiconductor alloy containing iron and semiconductor components, which enhances activation of nearby oxygen on irradiation of electromagnetic waves thereto. In addition, the present invention provides a combustion efficiency improving material, a plant growth promoting material, an aerobic microorganism activating material, an animal growth promoting and activating material, a muscle softening material, and a rust removing and preventing material, which contain the oxygen activating material therein.

In the oxygen activating method or the like according to the present invention, the electromagnetic waves irradiated to the alloy include electromagnetic waves with wavelengths of from 1 nm to 1 mm, preferably electromagnetic waves ranging from visible beams to far infrareds with wavelengths of from 380 nm to 1 mm. The electromagnetic waves irradiated include sunlight and white light.

The range of activation of oxygen influenced from the oxygen activating material according to the present invention depends on the amount of the iron-semiconductor alloy, the temperature condition, the humidity, and the wavelengths, amplitude, waveforms and intensity of the electromagnetic waves irradiated. The oxygen activating material, combustion efficiency improving material, plant growth promoting material, aerobic microorganism activating material and so forth according to the present invention may have shapes that are not specially limited but may be formed preferably in the shape of a plate or a foil.

The combustion efficiency can be improved for the reasons as considered below. Excitation of oxygen atoms weakens the intermolecular force and severs molecules. The severance widens the reaction area of an oxygen atom or molecule, thereby elevating the energy level and increasing the kinetic energy of an oxygen molecule. The severance between molecules and the increase in kinetic energy in this way may be thinkable causes to improve the efficiency of reaction with hydrogen and carbon atoms. The combustion efficiency thus improved can save fuels, lower carbon dioxide, and reduce various toxic substances (NOx, SOx, CO, HC and particulate substances) contained in exhaust gases.

The oxygen activating material according to the present invention also serves as the plant growth promoting material, the aerobic microorganism activating material, the animal growth promoting and activating material, and so forth for the reason as considered below. It can activate oxygen contained in a phosphoric acid reactive with ADP (adenosine diphosphate) on synthesis of ATP (adenosine triphosphate), which is a nucleotide for use in energy preservation and utilization, and activate oxygen for use in synthesis of the phosphoric acid.

That the oxygen activating material according to the present invention activates aerobic microorganisms is thinkably because the activated oxygen also activates hemoglobin and myoglobin that carry the activated oxygen.

A process of photosynthesis in plants comprises the following steps. (A) The energy of light absorbed in photosynthetic pigments activates chlorophyll—a much more. (B) The activated chlorophyll—a decomposes water molecules absorbed through roots into hydrogen and oxygen and synthesizes ATP from ADP and phosphoric acid. (C) Hydrogen and ATP produced in these reactions help carbon dioxide taken through stomata to react for synthesis of carbohydrate such as glucose. In this case, it may be considered that the oxygen activating material according to the present invention activates oxygen in the phosphoric acid for use in ATP synthesis or oxygen for use in synthesis of the phosphoric acid, thereby promoting the growth of plants.

The oxygen activating material according to the present invention can soften muscles, that is, improve the circulation of blood to loosen stiffness in the shoulder and relieve tension in the waist. This is also thinkably because the material helps activation of hemoglobin and myoglobin, and activation of the phosphoric acid for use in synthesis of ATP.

The oxygen activating material according to the present invention can remove rust and prevent occurrences of rust. This is thinkably because the material helps activation of oxygen atoms contained in water flowing in piping, and activation of oxygen molecules in impurities contained in water, such as silicon dioxide ($SiO_2$) and calcium carbonate ($CaCO_3$), which can form scales in water. In addition, activation of oxygen molecules contained in rust components, such as hydrated iron oxide (FeOOH) and triiron tetraoxide ($Fe_3O_4$), may be considered to remove rust and prevent occurrences of rust.

The iron-semiconductor alloy employed in the present invention can be produced through steel making with addition of a semiconductor such as silicon to the melt of iron. After completion of the steel making, the melt of iron is injected into a mold to form an ingot. The ingot is heated at about 1250° C., and then the properties of the alloy are established to produce a slab. The slab is next heated up to 1000° C. or higher, then gradually thinned to a thickness of several mm through hot rolling under load of about 2 ton/mm in the roll width to produce the iron-semiconductor alloy.

The oxygen activating material according to the present invention may be provided with a magnet on or in the vicinity of the opposite surface from the electromagnetic wave irradiated surface of the alloy. Alternatively, the electromagnetic wave irradiated surface of the alloy may be painted black. Further, the electromagnetic wave irradiated surface of the alloy may be provided with a photocatalytic agent applied thereon. Preferably, the oxygen activating material according to the present invention experiences a rust and corrosion preventive treatment chemically or physically applied to the surface thereof. The chemical rust and corrosion preventive treatment includes plating and physical evaporating. To the contrary, the physical rust and corrosion preventive treatment includes laminating with a film of synthetic resin such as polyester, or laminating with a glass plate, a transparent acrylic plate, a piece of stainless or copper foil. Before the chemical or physical treatment is executed, it is preferable to appropriately apply necessary treatments to the surface of the oxygen activating material. Such the application of rust and corrosion preventive treatment can prevent variations with time due to rusts, corrosions and erosions caused by getting in touch with humidity in the air and water.

When the oxygen activating material according to the present invention is located in the vicinity of an aimed target, it can exert a corresponding particular effect. For use as the combustion efficiency improving material, the oxygen activating material is located in the vicinity of a place for combustion, for example, a combustion engine or a combustion generator for heat. For use as the plant growth promoting material, the oxygen activating material is located in the vicinity of plants. For use as the aerobic microorganism activating material, the oxygen activating material is stuck onto a water tank for aerobic microorganisms. For use as the animal growth promoting and activating material, the oxygen activating material is stuck onto a wall of a breeding room for animals. For use as the muscle softening material, the oxygen activating material is stuck onto the skin over the tensioned muscle. For rust removing, the oxygen activating material is wound around the exterior of the rusted pipe.

EMBODIMENTS

An example of the oxygen activating material according to the present invention is described below. First, as the oxygen activating material according to the example, a thin plate of silicon iron (containing 87 wt. % or more iron, 6.5 wt. % or less silicon, and others such as 0.5 wt. % or less carbon, 1.5 wt. % or less manganese, 2.0 wt. % or less aluminum, 2.5 wt. % or less nickel and so on) was prepared. The oxygen activating material according to the example was employed to carry out experiments on improvement in the combustion efficiency, activity of aerobic microorganisms, promotion of the growth of plants, growth promotion and activity of animals, softening muscles, removal of rust and preventing occurrences of rust, as follows.

Experimental Example 1

(Combustion Efficiency Improving Material)

First, experiments were carried out when the oxygen activating material according to the example was employed as the combustion efficiency improving material. The oxygen activating material according to the example was cut out for preparation of 50 mm long×40 mm wide×0.1 mm thick samples. An automobile (registered in the first year of 1997 with a piston displacement of 2.981) was prepared as an experimental car. The combustion efficiency improving material according to the example was attached to the experimental car to measure the amount of fuel consumption and the rate of fuel consumption (fuel economy figure). The way of attachment of the combustion efficiency improving material according to the example and the driving time were varied to carry out experiments in the following four modes. In the first mode, the combustion efficiency improving material according to the example was prepared in the form of three sheets. The combustion efficiency improving material according to the example was attached to a location just beside the left-hand headlight of the experimental car. It was also attached to a location above the right-hand headlight in the bonnet (the place on which sunlight and light from the headlight irradiates). It was further attached to a location just the light for the rear license plate. Under such the condition, driving was performed in the daytime. These locations were the places on which lights from the headlight and others irradiated also on driving at night. In the second mode, the combustion efficiency improving material according to the example was attached to locations similar to those in the first mode. In addition, the combustion efficiency improving material attached was covered with a lightproof tape to prevent incidence of light thereto. Under such the condition, driving was performed in the daytime. In the third mode, the combustion efficiency improving material according to the example was attached to locations similar to those in the first mode, followed by driving at night with the headlights turned on. In the fourth mode, the combustion efficiency improving material according to the example was prepared in the form of three sheets. The combustion efficiency improving material according to the example was attached one by one to locations at both inner sides of the front glass of the experimental car. It was also attached to a location below the inner center of the rear glass, followed by driving in the daytime similar to the first mode. As a comparative mode, driving in the daytime was performed without the combustion efficiency improving material according to the example attached.

In these four modes and the comparative mode, after driving from the Hidaka interchange to the Ohme interchange on the Ken'ohdo expressway at a speed of 100 km/hour and returning while refueling at a gas station located 300 m away from the Hidaka interchange, the amount of fuel consumption was measured. All driving distance was 25.5 km. It was a fine weather and the relative humidity was 45-50%. On the basis of the amount of fuel consumption, the fuel economy figure (rate of fuel consumption) was calculated. The results are shown in Table 1.

TABLE 1

|  | Amount of Fuel Consumption (liter) | Rate of Fuel Consumption (km/l) | External Temperature (° C.) |
| --- | --- | --- | --- |
| First Mode | 2.00 | 12.75 | 19.0 |
| Second Mode | 2.32 | 10.99 | 20.0 |
| Third Mode | 2.26 | 11.28 | 20.0 |
| Fourth Mode | 2.17 | 11.75 | 19.0 |
| Comparative Mode | 2.58 | 9.88 | 19.0 |

Experimental Example 2

(Combustion Efficiency Improving Material)

Next, in the first through fourth modes of the experimental example 1 and the comparative mode, after driving from the Tokorozawa interchange to the Chichibu interchange on the Kan'etsu expressway at a speed of 100 km/hour and returning while refueling at a gas station located 4.5 km away from the Tokorozawa interchange along a general road, the amount of fuel consumption was measured. All driving distance was 108 km. It was a fine weather and the relative humidity was 45-50%. On the basis of the amount of fuel consumption, the fuel economy figure (rate of fuel consumption) was calculated. The results are shown in Table 2.

TABLE 2

|  | Amount of Fuel Consumption (liter) | Rate of Fuel Consumption (km/l) | External Temperature (° C.) |
| --- | --- | --- | --- |
| First Mode | 8.58 | 12.59 | 10.0 |
| Second Mode | 10.13 | 10.66 | 10.0 |
| Third Mode | 9.80 | 11.02 | 8.0 |
| Fourth Mode | 9.28 | 11.64 | 9.0 |
| Comparative Mode | 11.39 | 9.48 | 5.0 |

As obvious from Tables 1 and 2, it can be found that the amount of fuel consumption is lower and the rate of fuel consumption is higher when the combustion efficiency improving material according to the example is attached than when it is not attached. It can be also found that the amount of fuel consumption is lower and the rate of fuel consumption is higher even when no light is applied than when nothing is attached.

Experimental Example 3

(Aerobic Microorganism Activating Material)

Next, experiments were carried out when the oxygen activating material according to the example is employed as the aerobic microorganism activating material. To demonstrate the efficacy of the aerobic microorganism activating material according to this example, experiments were carried out on activation of not only aerobic microorganisms but also anaerobic microorganisms. Although the aerobic microorganism activating material according to the example can promote breeding of aerobic microorganisms that need oxygen in breeding, it may not promote breeding of anaerobic microorganisms that hardly need oxygen in breeding. In such the case, the material can be considered to activate oxygen. As the aerobic microorganism activating material according to the example was employed a sample similar to that used in the experimental example 1 and additionally provided with a lamination of a transparent polyester film with a thickness of 0.1 mm. First, rectangular parallelepiped water containers 1-4 (each 20-liters volume) were prepared to contain 18 liters of water and anaerobic green algae uniformly, followed by applying 3-liters per minute aeration to the containers. 1-4. This anaerobic green algae was collected from the Kinchakuda field at Komagawa in Saitama, Japan. The container 1 contained nothing but the anaerobic green algae. The container 2 was provided with the oxygen activating material according to the example, which was attached one by one onto two outer symmetrical surfaces of the container. The container 3 was supplied with 36 g of a compound microorganism formulation (ME-Bio available from Asahi Co., Ltd.) of an absolute aerobic microorganism fixed on diatom earth, which was housed in a chemical fibrous bag. The container 4 was supplied with the compound microorganism formulation, as in the container 3, and additionally provided with the oxygen activating material according to the example attached thereto, as in the container 2. In such the conditions, the containers 1-4 were spaced at an interval of 10 m and left stationarily for 5 days.

The states of the containers after 5 days were observed to find that the algae in the container 1 had hardly changed and the algae in the container 2 had blackened partly a little. The algae in the container 3 had blackened entirely, and the algae in the container 4 had blackened almost entirely and grayed here and there. That the algae in the container 2 blackens a little is thinkably because aerobic microorganisms in the air and the water are activated to decompose anaerobic microorganisms. If the oxygen activating material according to the example also influences on anaerobic microorganisms, the anaerobic microorganisms should not have blackened. That the algae in the container 3 blackens entirely is thinkably because aerobic microorganisms decompose the algae, which is anaerobic microorganisms. That the algae in the container 4 further grays is thinkably because activation of oxygen activates and breeds aerobic microorganisms to further decompose anaerobic microorganisms.

Halting the aeration and after leaving stationarily for 30 minutes, the transparency of water was observed to find that the container 4 was most excellent, then the transparency lowers in order of the container 3→the container 2→the container 1. The bulk of the entire algae was smallest in the container 4, then enlarged in order of the container 3→the container 2→the container 1.

Experimental Example 4

(Aerobic Microorganism Activating Material)

Further, experiments were carried out on the aerobic microorganism activating material according to the example. First, rectangular parallelepiped water containers 1-4 (each 20-liters volume) are prepared to contain 18 liters of human waste (wastewater from the flush lavatory of the inventor) therein, followed by applying 3-liters per minute aeration to the containers 1-4. The container 1 contained nothing but the wastewater. The container 2 was provided with the aerobic microorganism activating material according to the example, which is attached one by one onto two outer symmetrical surfaces of the container. The container 3 was supplied with 36 g of a compound microorganism formulation (ME-Bio available from Asahi Co., Ltd.) of an absolute aerobic microorganism fixed on diatom earth, which was housed in a chemical fibrous bag. The container 4 was supplied with the compound microorganism formulation, as in the container 3, and additionally provided with the oxygen activating material according to the example attached thereto, as in the container 2. Under such the conditions, the containers 1-4 were spaced at an interval of 10 m and left stationarily for 5 days.

The states of stain during the aeration after 5 days were observed to find that the cleanest was the container 4, then the others were stained in order of the container 3→the container 2→the container 1. Next, halting the aeration and after leaving stationarily for 30 minutes, the volume of settling sludge were observed to find that the least was in the container 4, then it increased in order of the container 3→the container 2→the container 1. The container 4 contained the largest volume of supernatant water, which was clearest. The supernatant water was stained in order of the container 3→the container 2→the container 1.

It is obvious from the above experimental examples 3 and 4 that the aerobic microorganism activating material according to the example activates oxygen, thereby activating only absolute aerobic microorganisms. The activated aerobic microorganisms decompose anaerobic microorganisms to improve decomposition of the algae and wastewater. Activation of oxygen activates hemoglobin and myoglobin that are oxygen carries in absolute aerobic microorganisms, thereby activating energy synthesis ATP (adenosine triphosphate). It thinkably activates cells and activates no anaerobic microorganisms but only absolute aerobic microorganisms.

Experimental Example 5

(Plant Growth Promoting Material)

Next, experiments were carried out when the oxygen activating material according to the example was employed as the plant growth promoting material. As the plant growth promoting material of the example was employed a sample similar to that used in the experimental example 1 and additionally provided with a lamination of a transparent polyester film with a thickness of 0.1 mm. Experimental targets were general green vegetables such as eggplant, tomato and green pepper, which was grown on the soil in a green house. In this case, the material was spaced one by one at an interval of about 5 m both in length and width as lateral checkers and hung from a height 2 m above the ground. As a result, harvests were improved about 10%.

In addition to the green vegetables, cut flowers such as rose, tulip and carnation, which were grown respectively on identical condition, were subjected to life tests. In the life tests of cut flowers, at first 20 sets of vases (water volume of several liters to several 10 liters), in which identical cut flowers were put respectively, were prepared. Ones of each 20 sets of vases were provided with the plant growth promoting materials according to the example, which were attached one by one onto two outer symmetrical surfaces of the vases. Others of each 20 sets of vases were not provided with the material. The vases, on which the material were attached, and the vases, on which the material were not attached, were spaced respectively at an interval of 20 m and left stationarily for 5-25 days in the respective flowering season. It was then confirmed that the life of the flowers of vases, on which the materials were attached, was elongated 30% or more than that of vases, on which the materials were not attached. It was confirmed that the green vegetables and cut flowers could be further improved when the surface of the oxygen activating material was always exposed to light.

Experimental Example 6

(Plant Growth Promoting Material)

Next, experiments were carried out on the plant growth promoting material for use in circulating water culture of spinach. A hydroponics device 450 mm long×450 mm wide× 250 mm high was employed. The upper fixative planting panel had 9 planting holes. The cultivation bath was supplied with 40 liters of a cultivating solution (Kind: Active, Cultivating Solution: Ohotsuka Chemistry A Formulation, pH 5.8, EC 2000 µS/cm, Concentration of Cultivating Solution: ¾). Six such the hydroponics devices were prepared. As the plant growth promoting material according to the example was employed a sample similar to that used in the experimental example 1 and additionally provided with a lamination of a transparent polyester film with a thickness of 0.1 mm. The plant growth promoting material according to the example was attached to three of the prepared six hydroponics devices and nothing was attached to the other three. Namely, three hydroponics devices (first through third modes) were arranged laterally in line. The plant growth promoting material according to the example was attached one by one onto two outer symmetrical surfaces of each hydroponics device to which sunlight was irradiated. The plant growth promoting material according to the example was attached to a rod as located 1 m above the second mode disposed at the center. The other three hydroponics devices (comparative modes 1-3) were arranged laterally in line at distances of 20 m apart from the first through third modes with the plant growth promoting material according to the example attached thereto. These hydroponics devices were each supplied with implantation of 9 spinach plants, followed by plantation for 28 days. After 28 days, spinach were collected from the hydroponics devices of the first through third modes and the comparative modes 1-3 by the numbers of plants shown in Table 3 (a total of 54 plants). After removal of the roots from the spinach, the weights of the remainder (stems and leaves) and the longest leaf lengths of the spinach were measured to calculate an average per hydroponics device. The results are shown in Table 3. In Table 3, the growth rate is a percentage of the average of the first through third modes to the average of the comparative modes 1-3.

TABLE 3

|  | Leaf Length (cm) | Plant Weight (g) | Number of Plants |
|---|---|---|---|
| First Mode | 26.2 | 73.5 | 9 |
| Second Mode | 27.9 | 75.1 | 9 |
| Third Mode | 27.3 | 74.6 | 9 |

TABLE 3-continued

|  | Leaf Length (cm) | Plant Weight (g) | Number of Plants |
|---|---|---|---|
| Average of Modes | 27.1 | 74.4 |  |
| Comparative Mode 1 | 22.4 | 58.4 | 9 |
| Comparative Mode 2 | 24.0 | 60.2 | 9 |
| Comparative Mode 3 | 24.3 | 60.9 | 9 |
| Average of Comparative Modes | 23.6 | 59.8 |  |
| Growth Rate (%) | 115 | 124 |  |

As obvious from Table 3, in comparison of the average of the first through third modes with the average of the comparative modes 1-3, the average of the first through third modes increases 15% in leaf length and 24% in plant weight relative to the average of the comparative modes 1-3.

Experimental Example 7

(Muscle Softening Material)

Next, experiments were carried out when the oxygen activating material according to the example was employed as the muscle softening material. As the muscle softening material was prepared a sample of the oxygen activating material according to the example, which was cut out in 15 mm long and wide×0.1 mm thick and additionally provided with a lamination of a transparent polyester film with a thickness of 0.1 mm. 30 panelists who suffered the symptom of stiffness in the shoulder were each given two sheets of the prepared muscles softening material, which were adhered one by one on the left and right shoulders by tapes, and 3 days later they were asked on the symptom. As a result, 13 panelists answered felt excellent, 11 panelists answered felt somehow good, 6 panelists answered felt nothing special, and no panelist answered felt worse. The persons who answered felt excellent and somehow good reach 80%. The muscle softening material can be adhered to various locations and is not required to worry about magnetic obstructions because it is not a magnet. As the polyester film is robust, the muscle softening material can be employed many times by changing the tape.

Experimental Example 8

(Animal Growth Promoting and Activating Material)

Next, experiments were carried out when the oxygen activating material according to the example was employed as the animal growth promoting and activating material. As the animal growth promoting and activating material according to the example was prepared a sample of the oxygen activating material according to the example, which was cut out in 50 mm long×40 mm wide×0.1 mm thick and additionally provided with a lamination of a transparent polyester film with a thickness of 0.1 mm. In this experimental example, 10 mice (Slc: ICR male mice aged 4 weeks) and 2 cages were prepared. In one cage, 2 sheets of the animal growth promoting and activating material were spread on the floor on which sawdust was spread. In the other cage, only sawdust was spread on the floor. Five mice were housed in each of the two cages, bred for 77 days in separate breeding rooms, and weighted every 7 days to calculate an average weight of the mice in each cage. Under the breeding condition including a room temperature of 23° C. and a lighting time of 12 hours/day, the feed (Solid Feed for Mouse/Rat: Rodent Diet EQ available from PMI Nutrition International) and city water were freely allowed to intake. The mice in the cage with the animal growth promoting and activating material spread therein is defined as an example and the mice in the cage without the material spread therein is defined as a comparative example to show the results in Table 4. In the table, the growth weight difference is shown as a value equal to the weight of the example minus the weight of the comparative example, and the growth rate is a percentage of the weight of the example to the weight of the comparative example.

TABLE 4

| Aged Weeks | Example (g) | Comparative Example (g) | Growth Weight Difference (g) | Growth Rate (%) |
|---|---|---|---|---|
| 4 | 19.4 | 19.6 | −0.2 | — |
| 5 | 31.5 | 29.1 | 2.4 | 108 |
| 6 | 35.0 | 32.6 | 2.4 | 107 |
| 7 | 37.9 | 35.3 | 2.6 | 107 |
| 8 | 39.5 | 37.0 | 2.5 | 107 |
| 9 | 41.2 | 38.7 | 2.5 | 106 |
| 10 | 43.1 | 40.5 | 2.6 | 106 |
| 11 | 44.8 | 42.6 | 2.2 | 105 |
| 12 | 47.5 | 44.7 | 2.8 | 106 |
| 13 | 48.7 | 46.2 | 2.5 | 105 |
| 14 | 51.0 | 47.9 | 3.1 | 106 |
| 15 | 52.9 | 49.3 | 3.6 | 107 |

As obvious from Table 4, the mice bred in the cage with the animal growth promoting and activating material spread therein grew faster than the mice bred in the cage without the material spread therein. It was also confirmed that the mice bred in the cage with the animal growth promoting and activating material spread therein were movable speedier and more active than the mice bred in the cage without the material spread therein.

Experimental Example 9

(Rust Removing and Preventing Material)

Next, experiments were carried out when the oxygen activating material according to the example was employed as the rust removing and preventing material. As the rust removing and preventing material were prepared six sheets of the oxygen activating material according to the example, which were each cut out in 1000 mm long×500 mm wide×0.1 mm thick and additionally provided with a lamination of a transparent polyester film with a thickness of 0.1 mm. The six sheets of the rust removing and preventing material were wound one by one around and fixed on a cooling water pipe (100 mm diameter) and a chilled-hot water pipe (80 mm diameter) of the absorption chiller-heaters, at the outer circumference of a supply pipe and a return pipe thereof located in the vicinity of the absorption chiller-heaters. They were similarly wound one by one around and fixed on a cooling water pipe of an open type crossflow cooling tower, at the outer circumference of a supply pipe and a return pipe thereof located in the vicinity of the tower. To irradiate the six wound sheets of the rust removing and preventing material always with light of about 10,000 luxes, white lights were set. The absorption chiller-heaters was manufactured in 1995 with a refrigerating capacity of 50 USRt, a cooling water retaining amount of 2 $m^3$, a chilled-hot water retaining amount of 1 $m^3$, a cooling water flow of 50 $m^3$/h, and a chilled-hot water flow of 30 $m^3$/h. As the make-up water, city water was employed. Chemicals for processing water were not employed. As the cooling water pipe and the chilled-hot water pipe, a carbon steel pipe for piping (White Pipe, JIS G 3452) was employed. A heat exchanger tube is made of copper.

On the day the rust removing and preventing material according to the example was attached to the absorption chiller-heaters, and one month, three months and six months later, the electric conductivity, the hydrogen ion exponent, and the concentration of iron and copper were measured. The make-up water supplied to the open type crossflow cooling tower was similarly measured. The results are shown in Table 5.

TABLE 5

|  | Electric Conductivity (μS/cm) | Hydrogen Ion Exponent (pH) | Iron (mg/l) | Copper (mg/l) |
| --- | --- | --- | --- | --- |
| Make-up water | 180 | 7.5 | Below 0.05 | Below 0.03 |
| The Day of Attachment | 1100 | 9.1 | 0.32 | 0.07 |
| One Month Later | 1140 | 9.0 | Below 0.05 | Below 0.03 |
| 2 Months Later | 1170 | 9.0 | Below 0.05 | Below 0.03 |
| 6 Months Later | 1110 | 8.9 | Below 0.05 | Below 0.03 |

As shown in Table 5, one-month running halted iron and copper ions to melt out and improved the rusted and corroded portions of the piping and machine in the cooling water system.

On the day the rust removing and preventing material according to the example was attached to the absorption chiller-heaters, and six months later, the covers were removed from the condenser and absorber in the absorption chiller-heaters to observe the improved condition of the heat exchanger tube plate, the improved condition in the heat exchanger tube, and the improved condition of scales attached to the filling and louver in the cooling tower. The results are shown in Table 6.

TABLE 6

|  | Situation observed on the day | Situation observed six months later |
| --- | --- | --- |
| Improvement in Heat exchanger tube plate (special steel) | Red rusts were here and there and gray scales attached and deposited too hard to remove with fingers. | Red rusts reduced to black rusts. Scales were softened and easily removable with fingers like a cream. |
| Improvement in Heat exchanger tube (of copper) | Blue corroded portions of copper arose. Hard and thin scales like cements attached and deposited on the inner surface. | Blue corroded portions of copper were improved. Scales were softened and easily removable with fingers like a cream. |
| Improvement in Scales attached to Filling and Louver in Cooling tower | Thin and hard scales attached particularly to the exterior. They can not be removed easily by rubbing them with fingers. | Scales were softened and removed easily by rubbing them with fingers. As this place contacts the external air, scales were repeatedly dried and wet. |

As the absorption chiller-heaters comprise a circulating closed circuit, water can not be replaced easily. Water was replaced on the day the rust removing and preventing material was attached. At that time, a large amount of contaminated red water was discharged. When water was replaced again three months later, a small amount of contaminated water was discharged. When water was replaced six months later, no contaminated water was discharged. Thus, large improvements in contamination of the steal pipe and the copper tube, and rust and corrosion thereof were confirmed.

Experimental Example 10

(Rust Removing and Preventing Material)

Further, experiments were carried out on the rust removing and preventing material according to the example that has a rust preventive property over the piping of the one-pipe system. As the rust removing and preventing material were prepared two sheets of the oxygen activating material according to the example, which were each cut out in 40 mm long×200 mm wide×0.1 mm thick and additionally provided with a lamination of a transparent polyester film with a thickness of 0.1 mm. A sheet of the rust removing and preventing material was wound around and fixed on the exterior of the piping with a diameter of 25 mm, which was located underground at the outdoor, extending from the meter in the city water meter box at the two-story house of the inventor. Another sheet was wound around and fixed on the exposed portion of the flush lavatory piping at the first story. Either was employed on condition that no electromagnetic wave such as light was irradiated to the surface of the rust removing and preventing material. The number of elapsed years of the piping was equal to 32 years during which no portion of the piping was updated. As the steel pipe was a galvanized steel pipe for water works (JIS G 3442), rust arose on the entire inner surface. On the day the rust removing and preventing material according to the example was fixed, and seven days, one month, three months and six months later, iron concentrations (mg/l) were measured on: (A) city water sampled to flow at the first time in the morning; (B) city water sampled when 20 liters flow after the first time; and (C) city water sampled at about 3 p.m. in the same day. Collections of water for water quality test were implemented at faucet in the kitchen spaced farthest from the meter. The results are shown in Table 7.

TABLE 7

|  | The day of fixation | 7 days later | One month later | 3 months later | 6 months later |
| --- | --- | --- | --- | --- | --- |
| A | 0.38 | 0.27 | 0.18 | 0.13 | 0.08 |
| B | 0.26 | 0.15 | 0.10 | 0.09 | 0.07 |
| C | 0.20 | 0.16 | 0.13 | 0.10 | Below 0.05 |

(mg/l)

As obvious from Table 7, the rust removing and preventing material according to the example has the rust removing and preventing effect. The city water piping in a common household is the one-pipe system that allows water to flow only in one direction. Thus, the rust preventing treatment hardly effects in comparison with the circulating piping though exertion of the rust preventing effect was easily confirmed without electromagnetic waves irradiated to the oxygen activating material.

The invention claimed is:

1. A method of causing an engine of a vehicle to consume less fuel, said method comprising:
    adding a semiconductor to molten iron during steel making, thereby providing an iron-semiconductor alloy;
    rolling the iron-semiconductor alloy under load, thereby providing a sheet;
    placing the sheet on the vehicle, proximate to the engine; and severely vibrating the semiconductor by irradiating the sheet with sunlight or white light having wavelengths of from 1 nm to 1 mm, thereby generating vibrating-electromagnetic waves as a result of electrochemical potentials being created across iron and semiconductor crystals of the sheet, and thereby enhancing vibrating-electromagnetic waves generated from the iron-semiconductor alloy and causing the engine to consume less fuel, wherein content of the semiconductor is 1-10 wt. % of the iron-semiconductor alloy and content of iron is 78-98 wt. % of the iron-semiconductor alloy.

2. A method of causing an engine of a vehicle to consume less fuel according to claim 1, wherein said semiconductor is silicon.

* * * * *

UNITED STATES PATENT AND TRADEMARK OFFICE
CERTIFICATE OF CORRECTION

| | | |
|---|---|---|
| PATENT NO. | : 8,079,346 B2 | Page 1 of 1 |
| APPLICATION NO. | : 11/916692 | |
| DATED | : December 20, 2011 | |
| INVENTOR(S) | : Yasuo Sakakura | |

It is certified that error appears in the above-identified patent and that said Letters Patent is hereby corrected as shown below:

Column 3, Lines 2-3 "AlN, A1As," should be -- A1N, A1P, A1As, --

Signed and Sealed this
Fifteenth Day of January, 2013

David J. Kappos
*Director of the United States Patent and Trademark Office*